United States Patent [19]

Kuwana et al.

[11] Patent Number: 5,031,449
[45] Date of Patent: Jul. 16, 1991

[54] ELECTROCHEMICAL DETECTOR FOR LIQUID CHROMATOGRAPHIC ANALYSIS OF CARBOHYDRATES

[75] Inventors: Theodore Kuwana; Juan Marioli; Javad M. Zadeii, all of Lawrence, Kans.

[73] Assignee: Shimadzu Corporation, Kyoto, Japan

[21] Appl. No.: 487,317

[22] Filed: Mar. 2, 1990

[51] Int. Cl.⁵ ............................................. G01N 15/00
[52] U.S. Cl. .................... 73/61.10 R; 204/294; 204/411; 422/70; 422/82.01; 422/82.03; 427/123; 427/126.1; 427/126.2; 427/126.3
[58] Field of Search ............... 73/61.1 C; 210/198.2, 210/656; 204/411, 294; 422/70, 82.01, 82.03; 427/123, 126.1, 126.2, 126.3

[56] References Cited

U.S. PATENT DOCUMENTS

4,877,694 10/1989 Solomon et al. .................... 429/42
4,975,172 12/1990 Yeager et al. ....................... 204/294

Primary Examiner—Hezron E. Williams
Assistant Examiner—W. Francos
Attorney, Agent, or Firm—Armstrong, Nikaido, Marmelstein, Kubovcik & Murray

[57] ABSTRACT

A highly sensitive and selective electrochemical detector has been developed for the liquid chromatograph analysis of carbohydrates. This detector includes copper particles and copper particles coated with copper oxide particles dispersed in a perfluorosulfonate ionomer film which is cast onto the surface of a glassy carbon electrode. The copper is electrochemically dispersed into the perfluorosulfonate ionomer by a constant potential method. The response of the detector is based on the electrolytic generation of a higher oxidation state species of copper catalytically oxidizing carbohydrates in alkaline solutions at a pH greater than 13.

7 Claims, 8 Drawing Sheets

ELECTROCHEMICAL DETECTOR FOR LIQUID CHROMATOGRAPHIC ANALYSIS OF CARBOHYDRATES

BACKGROUND OF THE INVENTION

Carbohydrates are energy-sustaining biomolecules which are an essential part of our diet and are important in monitoring and treating diseases such as diabetes. Thus, sensitive and selective methods for the quantitative analysis of carbohydrates are required.

Liquid chromatography has been used effectively for the separation of carbohydrates in conjunction with several spectrophotometric detection techniques. Such detection methods include refractive index and post-column fluorometric detection methods. Refractive index detectors inherently exhibit poor sensitivity and fluorometric detectors often require extensive chemical alteration of carbohydrates, to include stronger chromophores in their chromophoric poor structures.

In addition to these detectors, electrochemical detectors have been developed for the quantitative analysis of carbohydrates. For example, Johnson et al. Anal. Chim. Acta 1983, 149 1-10 and Chim. Acta. 1981, 132 11-22 have developed a pulse amperometric detector (PAD) that allows for the quantitative analysis of sugars and other compounds in highly basic solutions following high performance liquid chromatographic separations. The mechanism of such analysis relies on the adsorption of carbohydrates on gold or platinum electrodes and their subsequent electrocatalytic oxidation. Triple-pulse waveform detectors have attracted considerable attention and have become commercially available, but exhibit the following drawbacks: 1) the pulse detection mode has a high charging current that results in poor sensitivity as compared to the commonly used DC detection mode; and 2) the formation of oxide layers on the electrode surface requires continuous pulsing (surface reactivation) to maintain activity, sensitivity and stability.

Nickel oxide electrodes have been employed for detection of sugars in alkaline solution. The detection limit has been reported to be 1 ng for monosaccharides and 5 ng for oligosaccharides. Santos and Baldwin Anal. Chem. 1987 59 1766-1770 used a carbon paste electrode modified with cobalt phthalocyanine (COPC), an electron-transfer mediator. The COPC chemically modified electrode (CME) has a limited lifetime and requires periodic pulsation (activation). A solution phase redox reaction of copper bis(phenanthroline) with various sugars allows sensitive detection of these compounds at −75 mV vs. Ag/AgCl. However, the reaction requires elevated temperatures.

A recent chemically modified electrode for carbohydrate detection was reported by Prabhu and Baldwin Anal. Chem. 1989 61 852-856 and Anal. Chem. 1989 61 2258-2263. They describe a glassy carbon electrode on which a layer of crystalline $CuCl_2$ is deposited (a bare copper electrode). The lifetime of this electrode is 2-3 days, which is a marked improvement over COPC chemically modified electrode. The Cu-coated bare electrode offers enhanced sensitivity required for carbohydrate detection; however, the selectivity (aside from chromatographic resolution) and the long-term stability of such a catalytic electrode requires further improvement if it is to serve as a practical carbohydrate detector.

The present invention relates to a chemically modified electrode containing copper particles dispersed in a perfluorosulfonate ionomer sold under the trademark NAFION by du Pont. Polymer-coated chemically modified electrodes have been the subject of many ongoing investigations. For instance polymeric films of polyaniline serve as anchoring (nucleation) sites for platinum. Such particles are three-dimensionally dispersed into the polymer matrix. The advantages accrued from this type of electrode are mechanical stability and improved selectivity, which can be achieved by the controlled electrodeposition of metal into the polymer.

Films made of perfluorosulfonate ionomers, are quite inert in most electrolytes and adhere very strongly to substrates. Perfluorosulfonate ionomers have been used extensively as permselective coatings, sensors for incorporating cations, and charge exclusion membranes. The present inventors have found that a perfluorosulfonate ionomer deposited on glassy carbon and having copper and copper oxides electrolytically deposited into the ionomer is an electrode which can be successfully used as a working cell in a liquid chromatograph detector in qualitative analysis and quantitative analysis of carbohydrates.

SUMMARY OF THE INVENTION

The present invention relates to an electrode for use in the cell of a chromatographic detector for the analysis of carbohydrates. The electrode is composed of copper and copper particles coated with copper oxide which are dispersed or bound in a perfluorosulfonate ionomer. This electrode is sensitive to the carbohydrates due to the electrolytic generation of higher oxidation species of copper catalytically oxidizing the carbohydrates. The copper is dispersed in the ionomer by a constant potential method. Copper can also be deposited by other methods besides constant potentials as known by ordinary practitioners of the art.

BRIEF DESCRIPTION OF THE DRAWINGS

FIG. 2 shows the effect of deposition potential (a) and deposition time (b) on the amount (mol) of copper accumulated into the perfluorosulfonate ionomer.

with $1.0 \times 10^{31\ 4}$M of uric acid and ascorbic acid (b) and without such compounds (a).

DETAILED DESCRIPTION OF THE INVENTION

Controlled electrodeposition of copper in a perfluorosulfonate ionomer film results in catalytic sites containing copper and copper oxide which oxidize various carbohydrates in alkaline solutions of pH 13. The mechanical stability of the copper particles is greatly improved by incorporating the copper particles into a perfluorosulfonate ionomer polymeric film. Perfluorosulfonate ionomer also shows charge exclusion characteristics, thereby improving the selectivity of the electrode for carbohydrate detection. It also prevents poisoning and passivation of catalytic sites when analytes containing surfactants and other interferents are present. The parameters affecting the analytical performance of the electrode, such as the thickness of the perfluorosulfonate ionomer and the amount of copper loading, are optimized to fabricate a sensitive and stable electrode.

The perfluorosulfonate ionomer used in the present invention has the following repeating structure:

Similar Nafion-type structures are shown and described in Kirk Othmer, Encyclopedia of Chemical Technology, 3rd Ed., Supplemental Vol., Alcohol Fuels to Toxicology, pg. 559, herein incorporated by reference.

Batch and flow cell electrodes are prepared by first polishing glassy carbon electrodes, successively, with 1.0, 0.3 and 0.05 $\mu$m alumina containing solutions. The glassy carbon electrodes are thoroughly washed with distilled water, sonicated, washed with nanopure water (nanopure water is doubly deionized water) and then dried at either atmospheric temperatures or in oven at 60° C.

A perfluorosulfonate ionomer film is cast on the surface of the polished glassy carbon electrode by spread-coating, an alcoholic solution of perfluorosulfonate ionomer film on the surface of the glassy carbon electrode. The alcoholic solution contains approximately 1.0 to 2.5% of the ionomer and preferably 2.5%. Castings are made, preferably, from 5 $\mu$l of 2.5% solutions. The cast perfluorosulfonate ionomer aqueous solution is dried at room temperature or an oven at 60° C. to produce a film of about 2 $\mu$m.

Figure 1:
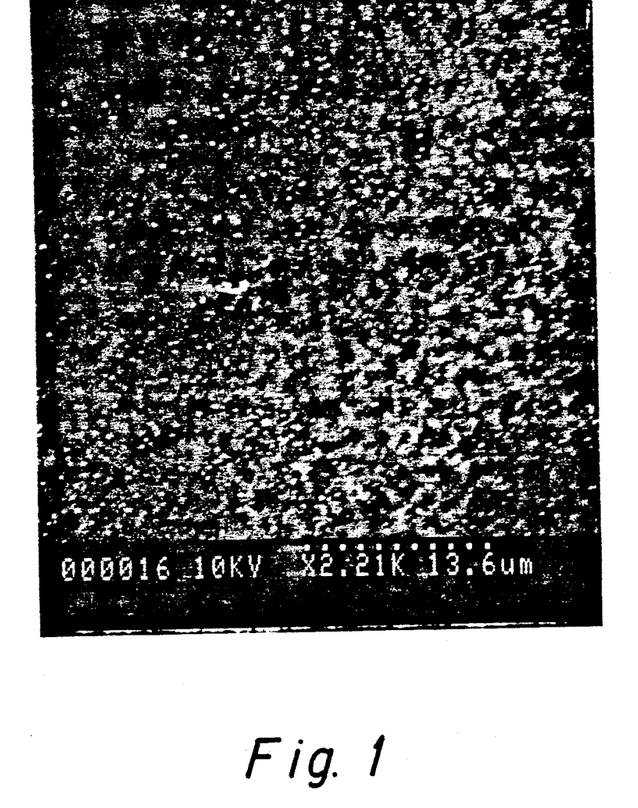
FIG. 1 is a scanning electron microscope photomicrograph of a copper-bound perfluorosulfonate ionomer coated glassy carbon electrode.

The electrode is then placed in an electrochemical cell containing copper salt solutions of 0.001 to 0.3 molar concentrations. This solution is stirred and subjected to an applied potential for approximately 5 to 100 seconds. The mechanism of copper electrode deposition involves nucleation and growth of copper particles through the polymer at the nucleation site. A photomicrograph of a perfluorosulfonate-coated electrode with electrodeposited copper is shown in FIG. 1. As shown, the copper particles are not uniformly dispersed on the glassy carbon surface. Within the perfluorosulfonate ionomer film relatively close nucleation sites having agglomerated particles and clusters of aggregated copper are seen that are non-crystalline. However, on a bare glassy carbon electrode the copper particles exhibit a three-dimensional growth behavior which results in a crystallite form. The spatial density of the copper particles, as compared with a non-perfluorosulfonate-coated glassy carbon is increased in the case of long electrodeposition time. Presumably, the copper nucleation sites coalesce within the perfluorosulfonate matrix to produce a continuous growth structure. However, nucleation sites on the bare electrode, i.e., the electrode not having a perfluorosulfonate ionomer coating tends to form crystallites which are less spatially dense compared to those on the perfluorosulfonate-coated glassy carbon for the same period of electrodeposition.

Figure 2A:
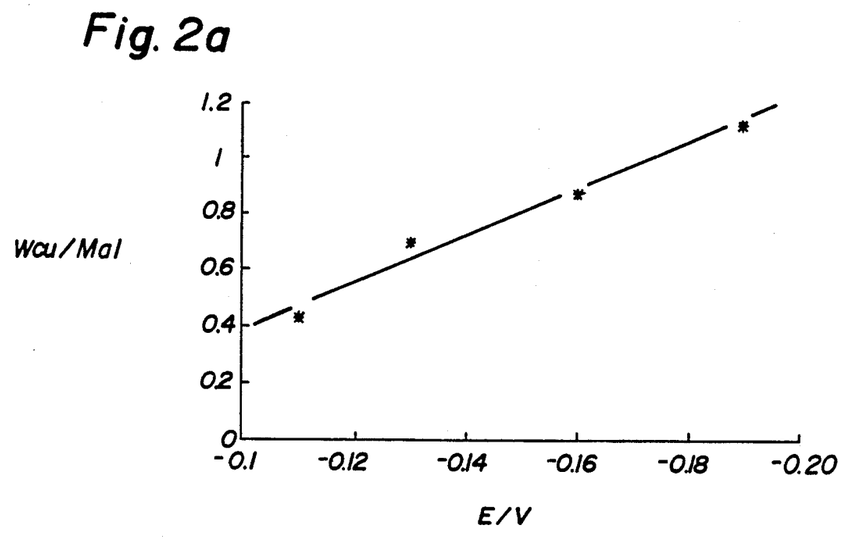

The relationship between the amount of copper loaded in the perfluorosulfonate-coated electrode, as a function of applied potential and electrolysis time is shown in FIG. 2. The amount of copper deposited into the polymer is related to the charge consumed during electrodeposition through the following equation:

$$W_{cu} = \frac{Q}{zF}$$

wherein $W_{cu}$ is the amount of copper in moles, and Q is the charge in coulombs. F is the Faraday constant and z is the charge of the copper ion. By changing the potential applied to a 0.3 molar solution of $Cu(NO_3)_2$, for a period of about 100 seconds, to a more negative potential (as shown in FIG. 2a) the amount of electrodeposited copper is increased. The results are reported in Table 1.

TABLE 1

| $W_{cu}$ in $\mu$mol | potential volts |
|---|---|
| 0.43 | −0.11 |
| 0.68 | −0.13 |
| 0.85 | −0.16 |
| 1.3 | −0.19 |

Figure 2B:
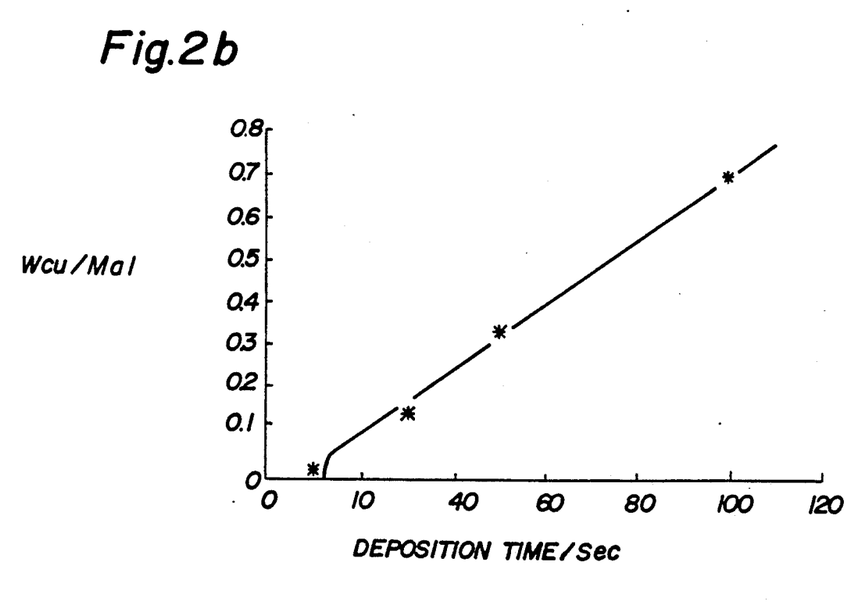

The duration of the applied potential is a second parameter that affects the amount of copper loading into the polymer. The number of moles of copper incorporated into the perfluorosulfonate ionomer from a 0.3 molar solution of $Cu(NO_3)_2$ as a function of electrolysis time at an applied potential of −0.1 V is shown in FIG. 2b. The results are shown in Table 2 below.

TABLE 2

| $W_{cu}$ in $\mu$mol | Deposit time in secs. |
|---|---|
| .12 | 30 |
| .32 | 50 |
| .68 | 100 |

EXAMPLE 1

The copper-bound perfluorosulfonate ionomer coated glassy carbon electrode (the scanning electron microscope photomicrograph of which is shown in FIG. 1) was prepared by casting onto a 3.0 mm polished glassy carbon electrode 4 $\mu$l of 0.25% perfluorosulfonate ionomer solution. The solution was dried at room temperature to produce a perfluorosulfonate film. Thereafter copper and copper oxide was deposited into the dry film by constant potential electrolysis at −0.07 V for two minutes from a $Cu(NO_3)_2$ solution at concentrations of $1 \times 10^{-2}$M. The electrode had a perfluorosulfonate film of 2 $\mu$m thickness and contains 0.1 $\mu$mol of copper.

Although longer electrodeposition times are recommended for higher sensitivity, a compromise between the deposition and coating thickness exists. The electrolysis time must be long enough to allow formation of copper nuclei, but not so long that the copper covers the perfluorosulfonate ionomer coating. The amount of copper in the perfluorosulfonate ionmer is strongly associated with the electrode background and noise level current. Table 3 summarizes the analytical performance of copper-bound electrodes employed in batch and flow cell processes.

TABLE 3

Analytical Performance of Copper-bound Electrodes[1]

| | Batch copper loadings | | Liquid Chromatography Flow-cell copper loadings | |
|---|---|---|---|---|
| | (0.06 μmol) | (0.17 μmol) | (0.04 μmol) | (0.26 μmol) |
| Background | 50.0 nA | 200.0 nA | 100.0 nA | 200.0 nA |
| Noise | 1.0 nA | 6.0 nA | 1.0 nA | 3.0 nA |
| Sensitivity[2] | 1.85 μA | 3.4 μA | 7.4 nA | 16.0 nA |

[1]perfluorosulfonate ionomer thickness 7 μm.
[2]Response to $1 \times 10^{-3}$ μM glucose for the batch and $1 \times 10^{-5}$ M glucose for flow cell.

Other conditions affecting the analytical performance of electrodes of the invention are discussed below. The equipment and reagents used to perform experiments and to obtain results are as follows:

Equipment

Cyclic voltammetric experiments were recorded with either a Bioanalytical Systems model CV1B potentiostat interfaced with a Houston Instruments model 2000 recorder or a Cypress Systems computer-aided potentiostat coupled to an Everex System 1800 AT computer. In the latter case, the graphic output was recorded on a Hewlett-Packard model HP-7440A plotter. The voltammetric cell was a 20 mL glass vial. The cell was joined to the glassy carbon working electrode (Bioanalytical Systems model MF-2012), a Ag/AgCl reference electrode (Bioanalytical Systems model RE-1) and a platinum wire auxiliary electrode.

The flow-injection and chromatographic systems (Shimadzu Scientific Instruments, Co., Columbia, Md.) consisted of pumps (LC-6A) equipped with high sensitivity pulse dampeners, a column oven (CTO-6A), an electrochemical detector (L-ECD-6A) and a recorder (CR-601). A glassy carbon electrochemical flow cell (Bioanalytical Systems model MF-1000) was used as the substrate for surface modification. For chromatographic separations, a 25 cm long, 5 mm i.d. Dionex HPLC-AS6 anion exchange column with a polymeric RP guard column (Brownlee Labs model GPP-013) was used. The scanning electron microscopy (SEM) photomicrographs were obtained with an Hitachi Model S-570 SEM.

EXPERIMENTAL SECTION

Reagents

Solutions of α-D(+)-glucose, D-sorbitol, D-mannitol, inositol, D-arabinose, sucrose, xylitol (Aldrich), α-lactose, maltose, α-L-rhamnose (Sigma), and fructose (Matheson Coleman and Bell) were prepared daily in Nanopure water. A solution of carbonate-free NaOH was prepared as the mobile phase for HPLC and FIA analysis. Nanopure water and the NaOH solutions were used to dilute analytes for HPLC and FIA analysis, respectively. Cupric nitrate, potassium nitrate, L-ascorbic acid, (Baker), uric acid and dopamine (Aldrich) were used as received from the suppliers identified.

EXAMPLE 2—Voltammetry

In order to determine which forms of copper species participate in the overall oxidation of carbohydrates, cyclic voltammetry was used to evaluate the mechanism of oxidation at the copper-bound perfluorosulfonate ionomer-coated glassy carbon electrode in alkaline solution, Prabhu et al. supra described a bare copper electrode i.e., a glassy carbon electrode modified with a layer of $CuCl_2$. This electrode was used for carbohydrate detection. Prabhu et al. attributed the carbohydrate oxidation to the redox couple Cu(II)/Cu(III), where copper acts as an electro-catalyst. In ascertaining the form of copper oxide which participates in the catalytic processes and the overall redox equilibrium for copper species in an alkaline solution, it is necessary to understand the catalytic processes involved in the carbohydrate oxidation.

Figure 3A:
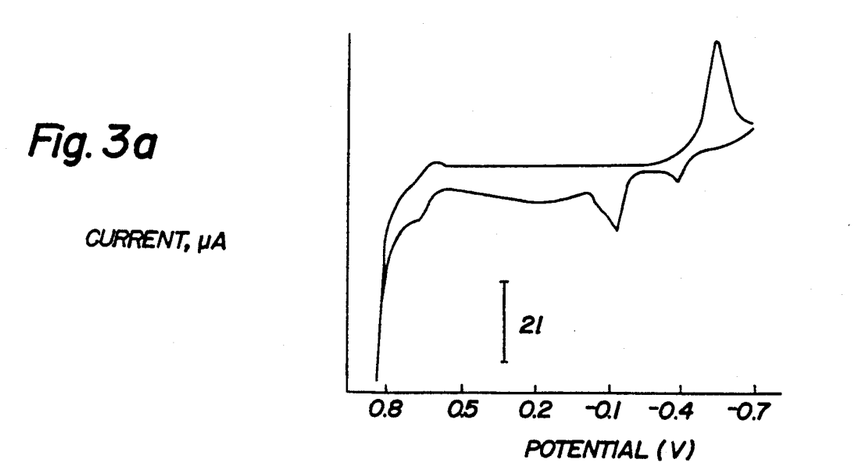
FIG. 3 shows cyclic voltammograms for a copper-bound perfluorosulfonate ionomer coated electrode recorded for a solution containing 0.15M NaOH (A), after five continuous cycles following (A) and (C) for $1 \times 10^{-3}$ M glucose following (B). Scan-rate 20 mV/s. Supporting electrolyte 0.15M NaOH.

Various forms of copper, such as metallic copper (either metallic copper or electrodeposited copper on glassy carbon) and copper salt (copper nitrate deposited on glassy carbon upon drying), were used to obtain cyclic voltammograms in an NaOH solution of pH 13. FIG. 3 illustrates a series of cyclic voltammograms obtained with the copper-bound perfluorosulfonate ionomer-coated electrode prepared in 0.15M NaOH following electrodeposition of copper from a $1 \times 10^{-2}$ μM copper nitrate solution at −0.7 V. The first cyclic voltammagrams (labelled A) exhibits distinct copper anodic peaks at −0.412, −0.166, 0.030, and 0.500 V vs Ag/AgCl. These peaks are related to the oxidation of surface electrodeposited copper. In the cathodic branch, two peaks appear at 0.56 and −0.60 V. If copper is deposited on the bare electrode (without perfluorosulfonate ionomer), the same cyclic voltammogram profile results. The redox equilibria of copper in an alkaline solution are complicated. The following half-cell reactions can be written:

| | $E^0_{298}$, volts |
|---|---|
| (1) $Cu_2O + H_2O + 2e^- = 2Cu^0 + 2OH^-$ | −0.58 |
| (2) $2Cu(OH)_2 + 2e^- = Cu_2O + 2OH + H_2O$ | −0.44 |
| (3) $Cu(OH)_2 + 2e^- = Cu^0 + 2OH$ | −0.30 |
| (4) $CuO_2^- + 2H_2O + e^- = Cu(OH)_2 + 2OH^-$ | +0.58 |

For clarity, the values of the half-cell potentials are given for each couple in terms of the standard reduction potentials. These values were corrected to denote potentials against a Ag/AgCl reference potential. The anodic transition of copper in alkaline solutions at a ring-disk electrode confirms that there are three distinct oxidative transitions for copper in an alkaline medium. However, the equilibrium potentials for the oxidation of copper [Cu(I), (II), (III)] are found to differ, mainly due to the presence of oxygen, which oxidizes the copper, and the disproportion reaction of $2Cu^+ = Cu^0 + Cu^{2+}$.

The fact that the cyclic voltammetric redox potentials are different than those shown above may also be due to the surface state of the metal. The Cu(II)/Cu(III) transition, which is believed to participate in the electrocatalytic oxidation of carbohydrates, is shown as a broad shoulder (inflection) on the oxidative current for the generation of oxygen. Such an oxidative current for Cu(III) is evident in FIG. 3A.

The anodic oxidation of copper metal (1.0 mm disk, 99.94% pure) gave well-defined and sharp peaks for Cu(I) and Cu(II) in alkaline solutions, but the Cu(II)/Cu(III) oxidative transition was not observable. The reason for the absence of the Cu(II)/Cu(III) transition in the oxygen evolution region may be due to the state of the metal surface [nucleation cluster vs. flat surface]. This is rather common for Cu(III) because of its strong oxidizing power. In contrast, the copper nitrate crystals immobilized on the glassy carbon gave stripping peaks similar to the copper-bound (electrodeposited) perfluorosulfonate ionomer glassy carbon electrode.

Figure 3B:
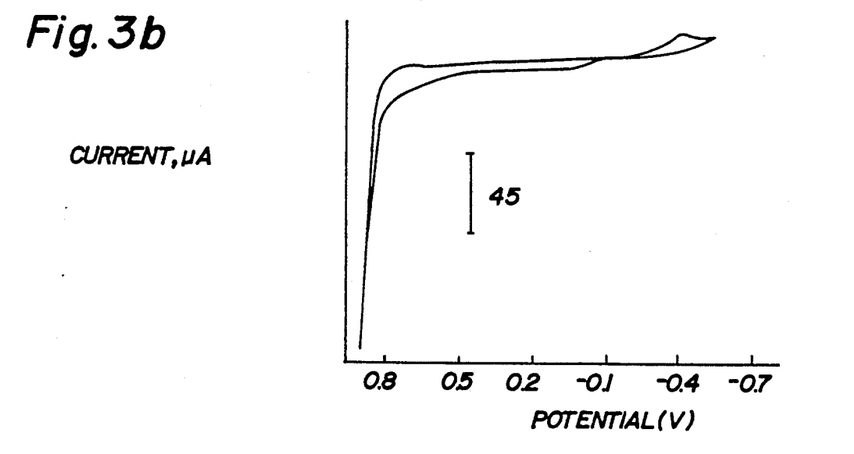
Figure 3C:
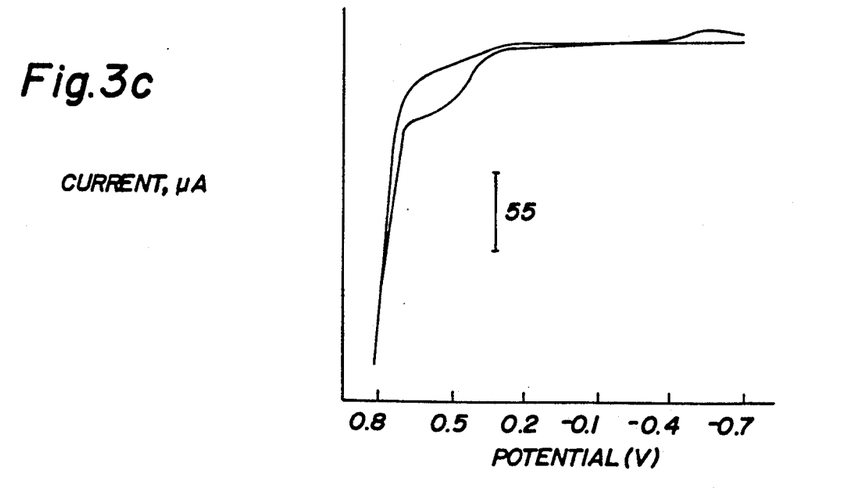

FIG. 3B shows the cyclic voltammogram (after continuous cycling for 8 min.) obtained with the copper-bound electrode in the NaOH solution. The cyclic voltammogram scan results in the disappearance of the copper oxidation peaks of Cu(I) and Cu(III) and a sharp decrease in the Cu(II) peaks. This indicates that the copper deposits are covered with a layer of oxides which hampers electrodissolution of copper from the "bulk". A scanning electron microscope photomicrograph of this electrode contains the same morphology as the scanning electron microscope photomicrograph of a freshly deposited copper glassy carbon electrode. The addition of 1.0 mM glucose to the NaOH solution yields a drawn-out anodic peak at 0.5 V associated with the oxidation of glucose (FIG. 3C). This potential is near the oxidative redox transition of Cu(II)/Cu(III).

As noted above, the copper (III) oxide peak is likely to be obscured or drawn out by the oxygen evolution peak under the high current density associated with high surface coverage (i.e., long deposition time). However, at low amounts of copper surface coverage (low loading) the voltammetric oxidation of glucose gives more detailed information about the redox behavior of glucose oxidation. This is more fully illustrated below.

EXAMPLE 3—Low Copper Loading

Figure 4:
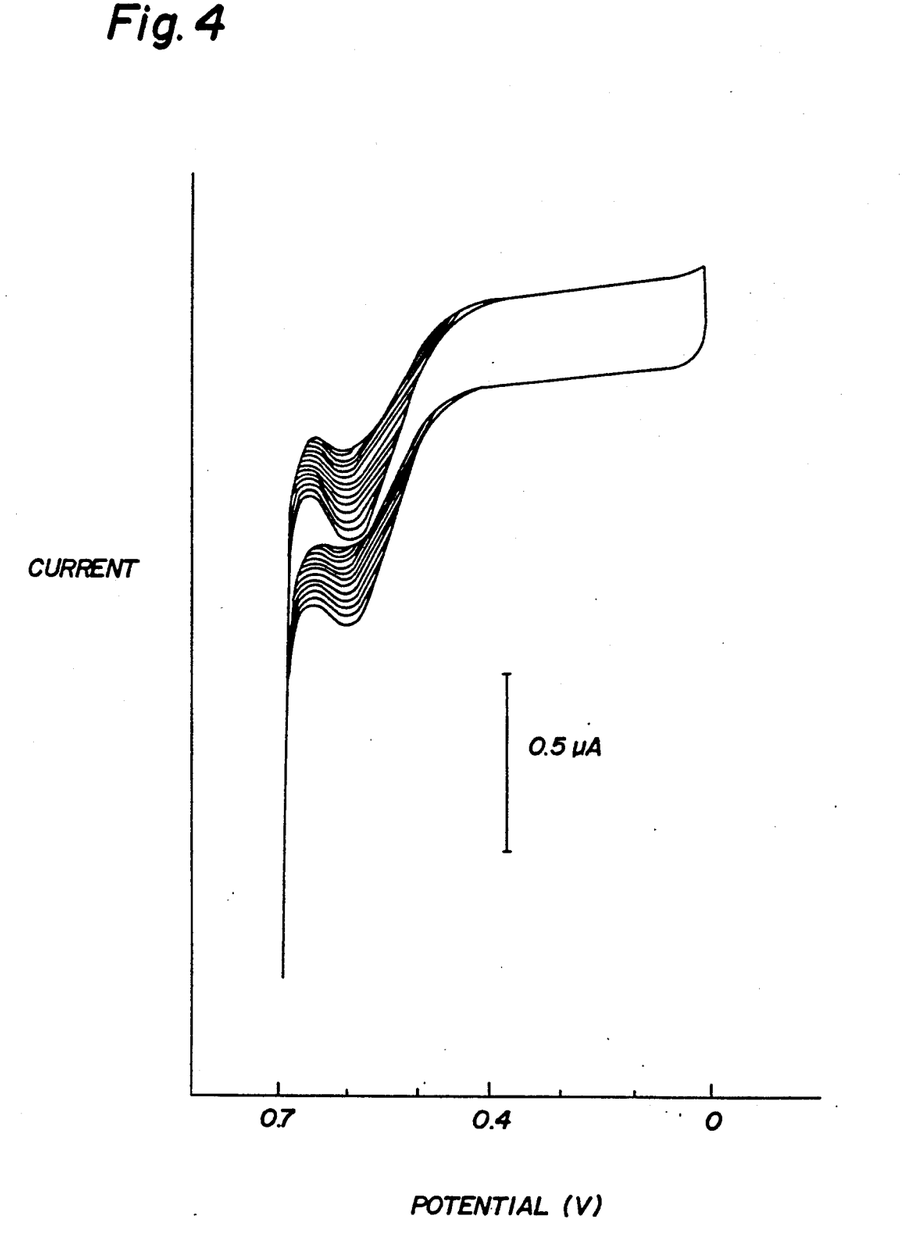
FIG. 4 shows repetitive cyclic voltammograms for $1 \times 10^{-3}$M glucose in 0.15M NaOH recorded at copper-bound, perfluorosulfonate ionomer-coated glassy carbon electrode.

FIG. 4 shows a set of repetitive cyclic voltammograms obtained with the copper-bound electrode in a $1 \times 10^{-3}$M glucose solution. To prepare low copper surface loaded electrodes, the copper deposition was facilitated by applying $-0.5$ V to the glassy carbon in a $1 \times 10^{-4}$M copper nitrate solution for 2 min. The anodic and cathodic peak currents for glucose appear to be more pronounced than the one obtained for the high surface loaded copper (see FIG. 3C). The catalytic peaks are separated by 0.0 V and peak currents decrease slowly upon continued scanning. Peaks are still observed, however, after 100 continuous cycles. The diminution of glucose redox peaks is related to the formation of copper oxide. This behavior was also seen in the case of the copper-bound, perfluorosulfonate-coated glassy carbon in a NaOH solution (see FIG. 3B). Thus, low amounts of copper loading in the perfluorosulfonate gives rise to low current density in which voltammetric peaks due to glucose oxidation can easily be seen.

The electrocatalytic oxidation of sugar requires an alkaline solution with pH of 13 or greater. There is a sharp decrease or complete absence of glucose voltammetric response upon decreasing the pH of the NaOH solution, or when assayed in a sodium borate buffer of pH 7.0–9.0, or in phosphate buffer solution at physiological pH. For this reason, a 0.15M NaOH solution of pH 13 was used throughout for the carbohydrate determinations.

EXAMPLE 4—Chromatography

Figure 5:
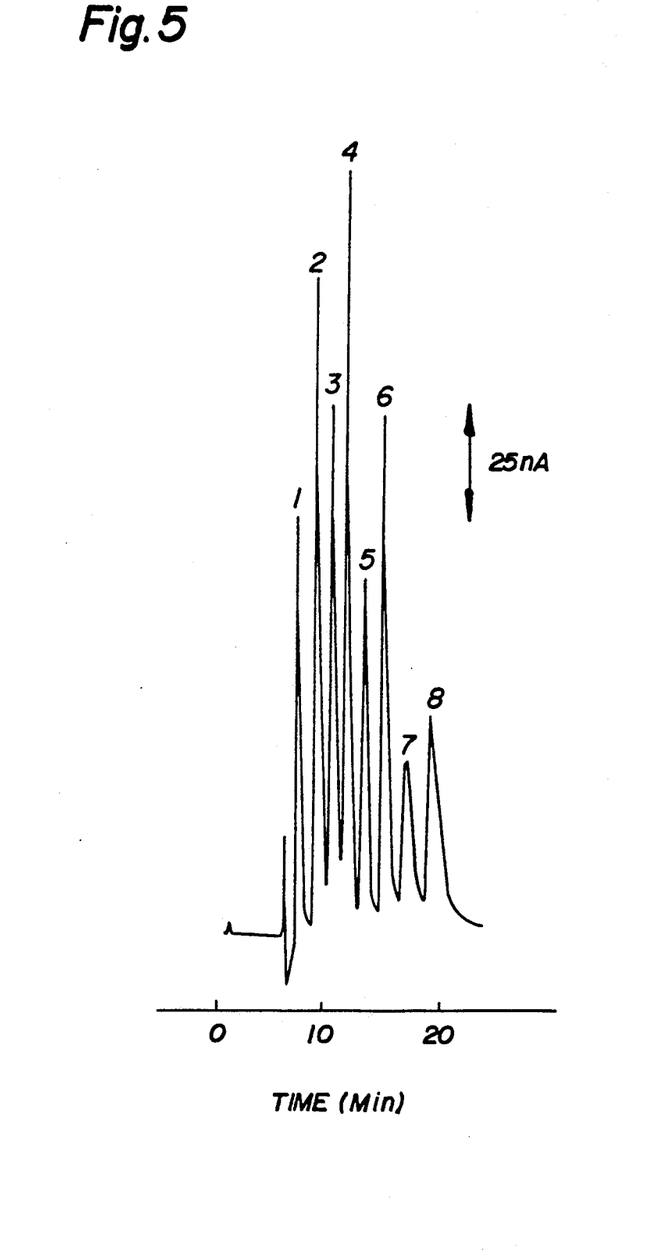
FIG. 5 shows chromatograms of mixtures of carbohydrates.

The copper-bound chemically modified electrode seems to be a viable amperometric detector for on-line, flow-through analysis, including LC and FIA. To explore the advantages of this detector with respect to stability, sensitivity and selectivity, several experimental results are presented. FIG. 5 shows the chromatogram for a sample mixture of sugars containing both mono- and disaccharides i.e., containing (1) inositol, (2) sorbitol, (3) rhamnose, (4) arabinose, (5) glucose, (6) ribose, (7) lactose and (8) sucrose. Carbohydrate concentrations: $3 \times 10^{-4}$M (1,2,4) $2 \times 10^{-3}$M (3,5,7,8) and $5 \times 10^{-3}$M (6). Injection volume 20 $\mu$L. Flow rate 0.3 mL/min. Applied potential 0.48 V. Mobile phase 0.15M NaOH. The effective chromatographic separation is indicated by excellent resolution, capacity factor 0.18–1.9, at the low flow rate (0.3 mL/min). The separation of these sugars at 1.0 mL/min results in co-elution and unresolved peaks (i.e., capacity factors ranging from 0.14 to 1.5). In addition, a substantial decrease in the sensitivity (S/N ratio) of the peaks is recorded at high flow rates.

The isocratic analysis of many carbohydrates in alkaline solution following anion exchange separation yields unresolved peaks which are mainly due to nearly identical disassociation constants. The efficient separation of many sugars in an anion exchange column can be facilitated by the application of a pH gradient. This would normally complicate the separation procedure and prolong the overall analysis time. Compared to gradient elution, the use of isocratic separation at a low flow rate improves the separation methodology for carbohydrate determination. Correspondingly, the sensitivity of the copper-bound electrode increases with a decrease in mobile phase flow rate. Similar effects have been reported by Prabhu et al. supra in which an exponential decay in glucose response was observed upon an increase in the liquid chromatographic mobile phase flow rates. Unlike other generic amperometric detectors, where mass transport to the electrode increases as a function of the flow rate, the kinetics of the electrocatalytic reaction of the copper-bound perfluorosulfonate glassy carbon with carbohydrates appears to be very slow to generate high currents at high flow rates.

Hydrodynamic voltammograms (HDVs) can be constructed to determine the set potential for carbohydrate detection. The HDVs, obtained under flow injection analysis, for the carbohydrate detector illustrate a peak-shaped profile with a maximum response at about 0.55 V. However, a significantly lower set potential can be chosen to obtain an improved signal-to-noise ratio. On the basis of this study, it was determined that a set potential of 0.48–0.50 V vs Ag/AgCl would suffice for the amperometric liquid chromatographic detection of all carbohydrates tested to date.

EXAMPLE 5

Figure 6:
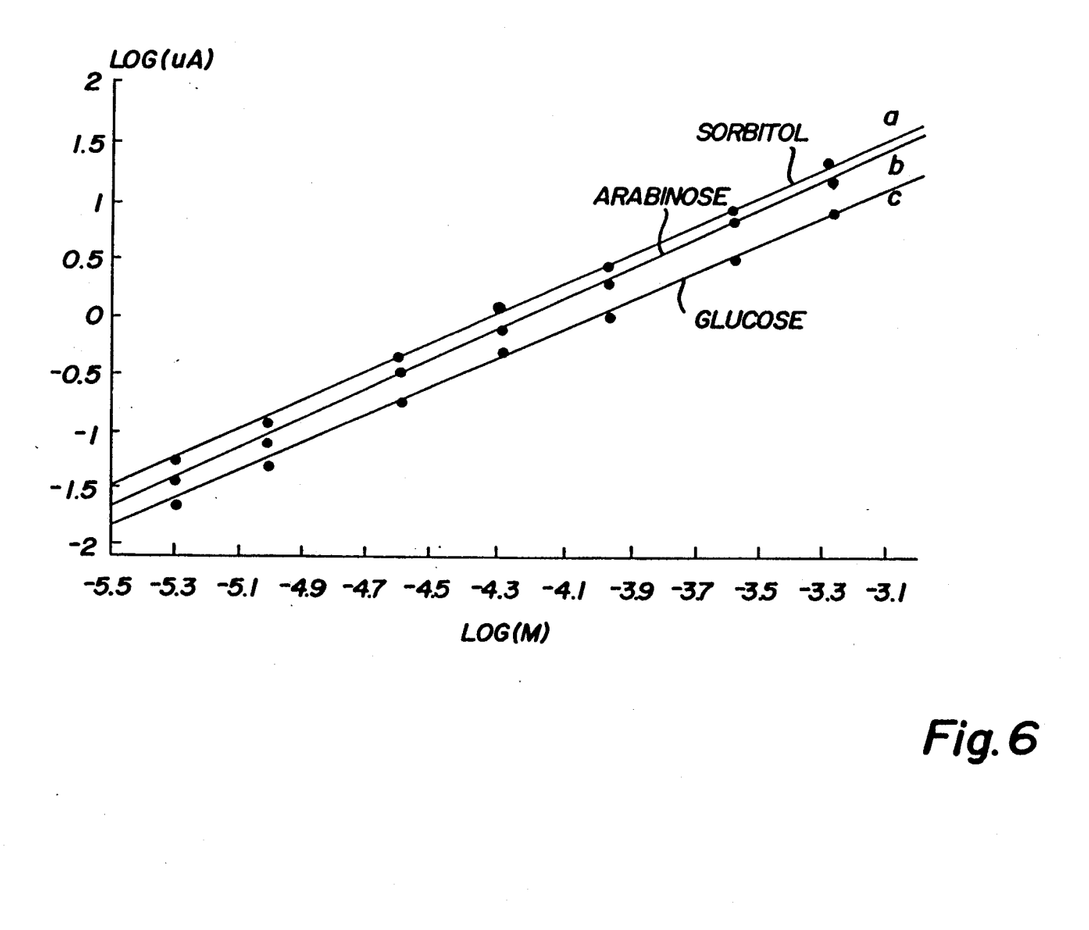
FIG. 6 shows chromatographic calibration plots obtained for solution of increasing carbohydrate concentrations.

The analytical usefulness of copper-bound electrodes for carbohydrate analysis is based primarily upon the linearity and reproducibility of the response. Such an electrode exhibits a concentration-dependence profile that is well-defined and reproducible. In FIG. 6, the chromatographic responses at flow rates of 0.7 mL/min of sorbital (So,a), arabinose (Ar,b) and glucose (Gl,c) are shown with a series of six concentration increments from $5 \times 10^{-6}$M to $1 \times 10^{-3}$M. The current vs. concentration plots yielded linear responses with slopes (log μA/log M) of 1.29 (So), 1.24 (Ar) and 1.22 (Gl); intercepts (log μA) of 5.46 (So), 5.39 (Ar) and 4.95 (Gl); and correlation coefficients of 0.99 (So,Gl) and 0.992 (Ar). The fact that different intercepts are observed may be related to the degree of ionization of each carbohydrate in an alkaline solution. These sugars have $pK_a$ values which are 13.6 (So), 12.34 (Ar) and 12.28 (Gl). The perfluorosulfonate ionomer coating may have some impact on the sensitivity of these carbohydrates. Carbohydrates with higher $pK_a$ values (lower ionization tendency) produce a higher response for the same concentration. Perfluorosulfonate ionomer film in turn, tends to attract neutral to cationic species to the electrode. Because at pH 13 most carbohydrates are in the anionic form, a substantial charge exclusion behavior may be the dominant factor for rejection of carbohydrates from the electrode. It is believed that the carbohydrates with low ionization constants will be attracted to the electrode, therefore showing much more sensitivity. The role of electron transfer rate constants is another factor which may contribute to the overall sensitivity, but these values are not available at this time.

Because of the effective copper dispersion on the perfluorosulfonate ionomer-coated glassy carbon electrode, very low detection limits were obtained following on-column injection of various carbohydrates. The detectability was estimated for arabinose, glucose, fructose, rhamnose, maltose and lactose. The detection limits, calculated from 3 times the noise, were found to be 10, 20, 30, 60, 100 and 120 pmol, respectively. The bare copper electrode described by Prabhu et al. supra gives much lower detection limits than the perfluorosulfonate ionomer-coated electrode of the invention. For example, glucose can be detected at 1 pmol. Such results, however, were offset by lower stability. Perfluorosulfonate ionomer provides better stability and reproducibility than a bare copper electrode.

EXAMPLE 6

The catalytic oxidation of carbohydrates in general, and of glucose in particular, results in reproducible chromatographic responses. For 100 successive on-column measurements of $1 \times 10^{-3}$ M glucose over 18 hr, the relative standard deviation (R.S.D) was 4.5%. The response of the copper-bound perfluorosulfonate ionomer electrode to carbohydrates remains stable for many hours. The lifetime (longevity) of the electrode was determined by loading different amounts of copper on the electrode as monitored by the electrodeposition period. For example, an electrode (in a chromatographic flow cell) was prepared on which copper was accumulated from a 0.3M $Cu(NO_3)_2$ solution for 10 s at $-0.7$ V. The response of this electrode remained stable for many days, during which the chromatographic response of glucose remained within 90-95% of its original (first hour) response level (over 60 injections made per day). However, after six days, the response slowly decreased to approximately 60% of its original response. Although the response decreased, a stable signal could still be attained with a well-defined calibration plot. On the other hand, with low copper loading, a deposition for 2 s from 0.3M $Cu(NO_3)_2$ resulted in a reproducible signal (5.10% RSD) for only two days. The chromatographic response of glucose tends to go down after the second day by 50% as compared to the first day's response.

The analysis of chromatographic eluant from the cell by atomic absorption spectrometry showed a low level of copper (2 ppm). It is presumed that the copper is leached mechanically or oxidatively from the electrode surface. Thus, the amount of accumulated copper nuclei on the electrode determines its useful lifetime. The loss of copper from the polymer matrix may be the main reason for the decrease in sensitivity and stability of the copper-bound electrode. Although the presence of perfluorosulfonate ionomer slows down the rate of copper loss, it does not completely eliminate it.

EXAMPLE 7—Analytical Utility

Figure 7:
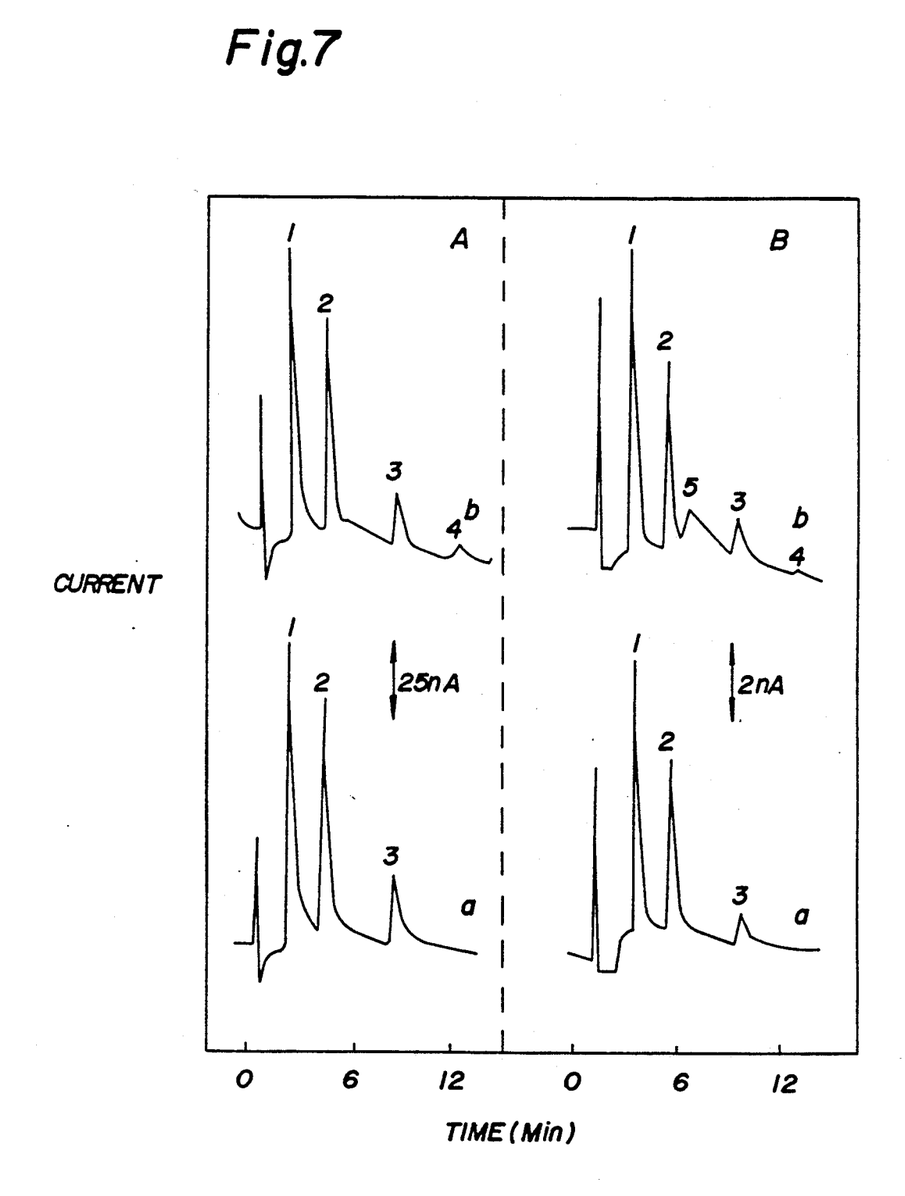
FIG. 7 shows chromatograms for $5 \times 10^{-4}$M (1) mannitol, (2) glucose, (3) sucrose, (4) ascorbic acid and (5) uric acid, obtained at a copper-bound perfluorosulfonate ionomer film coated on a glassy carbon electrode (A) a copper containing glassy carbon electrode (B)
Figure 8A:
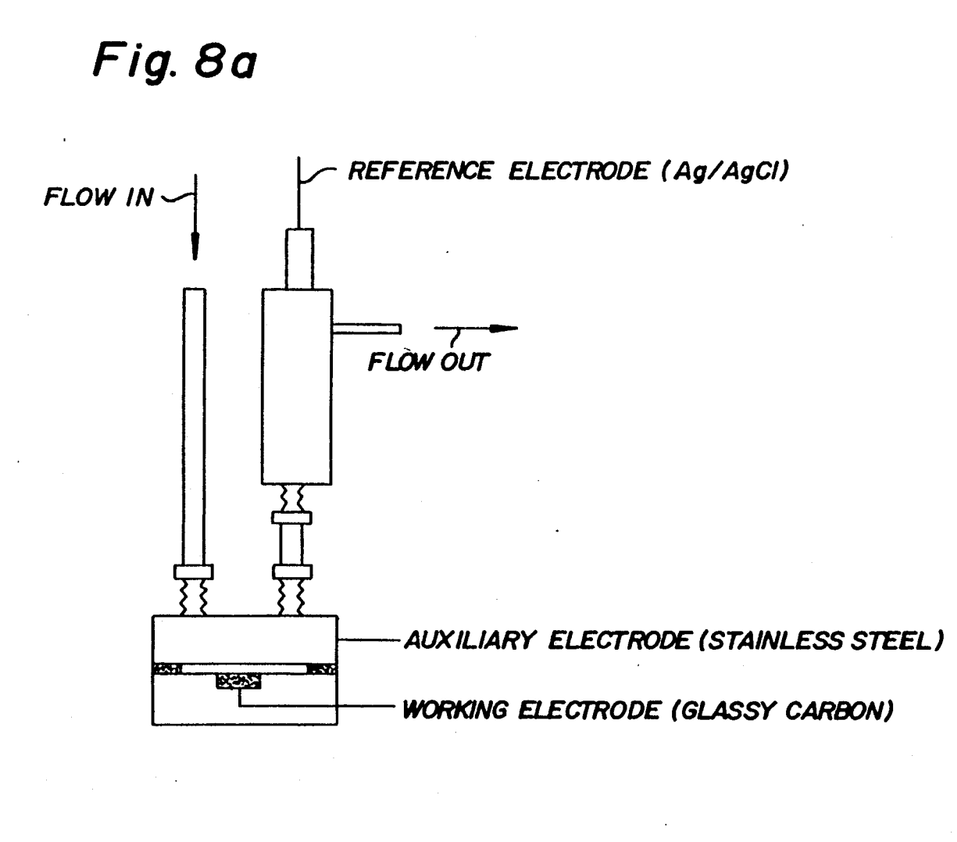
FIG. 8 shows a chromatographic flow cell which incorporates perfluorosulfonate isomer and copper onto a glassy carbon electrode.
Figure 8B:
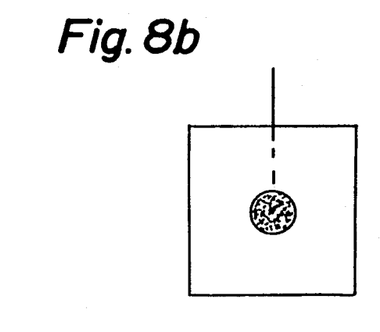
Figure 8C:
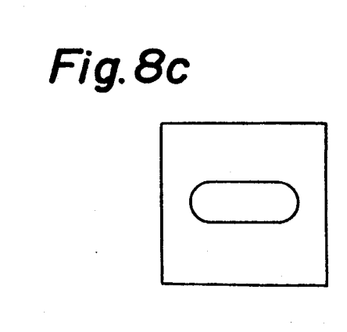

The ability of the copper-bound electrode with perfluorosulfonate ionomer coating to detect carbohydrates and simultaneously exclude uric acid is demonstrated in FIG. 7. With the perfluorosulfonate ionomer-coated electrode (A) and the bare electrode (B), sugars such as mannitol, glucose and sucrose can be detected (see chromatograms a). Both electrodes offer excellent resolution and sensitivity at low flow rate (0.3 mL/min). A subsequent addition of $1 \times 10^{31}$ $^4$M uric acid and ascorbic acid to the mixture of carbohydrates yields an additional peak, peak 4, [chromatogram A(b)] due to catalytic reaction of ascorbic acid at the perfluorosulfonate ionomer-coated copper electrode. In contrast, the response of the bare copper electrode [chromatogram B(b)] to the mixture results in two peaks 4 and 5. Both uric acid and ascorbic acid are detected after separation. It can be concluded that only uric acid is rejected from the perfluorosulfonate ionomer-coated electrode, while ascorbic acid (i.e., an acidic sugar, $pK_1=4.03$, $pK_2=11.34$) is partially detected at both coated and bare copper electrodes. The reason for the low sensitivity of ascorbic acid with both electrodes at $1 \times 10^{-4}$M is consistent with the previous explanation that carbohydrates with low $pK_a$ tend to have low sensitivity (i.e., smaller slope). The selectivity of this type of electrode, based on charge exclusion, improves the amperometric detection of carbohydrates. As a result, the diffusive mass-transport of uric acid to the electrode (glassy carbon) is impeded by the perfluorosulfonate ionomer coating, while carbohydrates can be detected at both the coated and bare copper electrode.

One of the problems with the use of a polymer-coated electrode for flow-through systems is the finite loss of the film or gradual change in the mechanical integrity of the perfluorosulfonate film. It is difficult to maintain an invariant structure, chemically and physically throughout the lifetime of the film. However, the addition of an internal standard periodically for calibration purposes will correct any change in the electrode sensitivity to the analyte carbohydrates. Another advantage of the perfluorosulfonate ionomer coating becomes apparent with regard to the stability of copper on the glassy carbon electrode surface. The bare copper-bound electrode tends to lose copper faster than that an electrode first coated with a perfluorosulfonate ionomer. Such a characteristic was obtained when electrodes with and without perfluorosulfonate ionomer were tested for long-term stability. The bare electrode tends to have a shorter lifetime than the perfluorosulfonate ionomer-coated electrode.

CONCLUSION

Carbohydrates are not easily oxidized and, hence, are not easily detected at solid electrodes, such as platinum, gold or glassy carbon, by constant potential (amperometric) methods due to slow electron transfer kinetics. The novel electrode described herein, containing copper particles dispersed in a perfluorosulfonate ionomer on glassy carbon, overcomes the kinetic limitation by a catalytic process which substantially lowers the overpotential for the oxidation reaction. This catalysis provides sensitivity and specificity and prolonged life. The mechanical stability of the copper is greatly improved by incorporation into the polymeric film. Perfluorosulfonate ionomer also provides a barrier to anionic species reaching the catalytic copper sites, thereby adding a new dimension to selectivity in liquid chromatograph electrical detection analysis. Other advantages are the low cost and relative ease of preparation of the detector.

We claim:

1. An electrode, comprising:
    a) a glassy carbon substrate;
    b) a surface of the glassy carbon substrate coated with a perfluorosulfonate ionomer; and
    c) copper and copper oxide particles electrochemically incorporated into the perfluorosulfonate ionomer.

2. The electrode of claim 1 wherein the copper and copper oxide particles are randomly dispersed in the perfluorosulfonate ionomer.

3. The electrode of claim 1, wherein the perfluorosulfonate ionomer coating is 2 to 10 $\mu$ meters thick.

4. The electrode of claim 2, wherein the amount of copper present in the perfluorosulfonate ionomer coating is between 0.1 to 0.25 $\mu$ mol.

5. The electrode of claim 2, wherein the copper and copper oxide particles are approximately 1 $\mu$m to 3 $\mu$m.

6. In a high performance liquid chromatographic assay for the analysis of carbohydrates, the improvement comprising:
    using a detector comprising a glassy carbon substrate having on a surface thereof a perfluorosulfonate ionomer coating and particles of copper and copper oxides electrochemically incorporated into the perfluorosulfonate ionomer.

7. In a chromatographic apparatus for the analytical detection of carbohydrates including an injector, a column and a detector, the improvement comprising a detector comprising a glassy carbon substrate having on a surface thereof a perfluorosulfonate ionomer coating and particles of copper and copper oxides electrochemically incorporated into the perfluorosulfonate ionomer.

* * * * *